(12) United States Patent
Raymond et al.

(10) Patent No.: US 9,603,699 B2
(45) Date of Patent: Mar. 28, 2017

(54) NON-INVASIVE REFRACTIVE TREATMENT USING NANOPARTICLES

(71) Applicant: AMO WaveFront Sciences, LLC, Santa Ana, CA (US)

(72) Inventors: Thomas D. Raymond, Edgewood, NM (US); Richard J. Copland, Albuquerque, NM (US)

(73) Assignee: AMO Wavefront Sciences, LLC, Santa Ana, CA (US)

( * ) Notice: Subject to any disclaimer, the term of this patent is extended or adjusted under 35 U.S.C. 154(b) by 0 days.

(21) Appl. No.: 14/971,861

(22) Filed: Dec. 16, 2015

(65) Prior Publication Data
US 2016/0101045 A1 Apr. 14, 2016

Related U.S. Application Data

(63) Continuation of application No. 14/199,766, filed on Mar. 6, 2014, now Pat. No. 9,241,901.

(60) Provisional application No. 61/794,070, filed on Mar. 15, 2013.

(51) Int. Cl.
| | |
|---|---|
| *A61F 9/01* | (2006.01) |
| *A61F 9/007* | (2006.01) |
| *A61K 9/00* | (2006.01) |
| *A61F 2/14* | (2006.01) |
| *A61K 33/24* | (2006.01) |

(52) U.S. Cl.
CPC .............. *A61F 2/14* (2013.01); *A61F 2/145* (2013.01); *A61F 2/147* (2013.01); *A61K 9/0048* (2013.01); *A61K 33/24* (2013.01); *A61F 2250/0067* (2013.01); *A61K 9/0051* (2013.01)

(58) Field of Classification Search
None
See application file for complete search history.

(56) References Cited

U.S. PATENT DOCUMENTS

| 4,461,294 A | * | 7/1984 | Baron | A61F 9/008 606/5 |
|---|---|---|---|---|
| 5,779,696 A | | 7/1998 | Berry et al. | |
| 6,537,545 B1 | | 3/2003 | Karageozian et al. | |
| 2004/0199149 A1 | | 10/2004 | Myers et al. | |
| 2010/0210996 A1 | * | 8/2010 | Peyman | A61F 7/007 604/20 |
| 2014/0171927 A1 | * | 6/2014 | Depfenhart | A61N 5/062 606/5 |

FOREIGN PATENT DOCUMENTS

| WO | 2009143054 A2 | 11/2009 |
|---|---|---|
| WO | 2011112582 A2 | 9/2011 |

OTHER PUBLICATIONS

Nagy (Nagy, L.J., et al., Potentiation of Femtosecond Laser Intratissue Refractive Index Shaping (IRIS) in the Living Cornea with Sodium Fluorescein, Investigative Ophthalmology & Visual Science, Feb. 2010, vol. 51, No. 2).*
International Search Report and Written Opinion for Application No. PCT/US2014/021359, mailed on May 21, 2014, 12 pages.

* cited by examiner

*Primary Examiner* — H. Sarah Park
(74) *Attorney, Agent, or Firm* — Abbott Medical Optics Inc.

(57) ABSTRACT

Embodiments of this invention generally relate to systems and methods for optical treatment and more particularly to non-invasive refractive treatment method based on sub wavelength particle implantation. In an embodiment, a method for optical treatment identifies an optical aberration of an eye, determines a dopant delivery device configuration in response to the optical aberration of the eye, wherein the determined dopant delivery device is configured to impose a desired correction to the eye to mitigate the identified optical aberration of the eye by applying a doping pattern to the eye so as to locally change a refractive index of the eye.

19 Claims, 7 Drawing Sheets

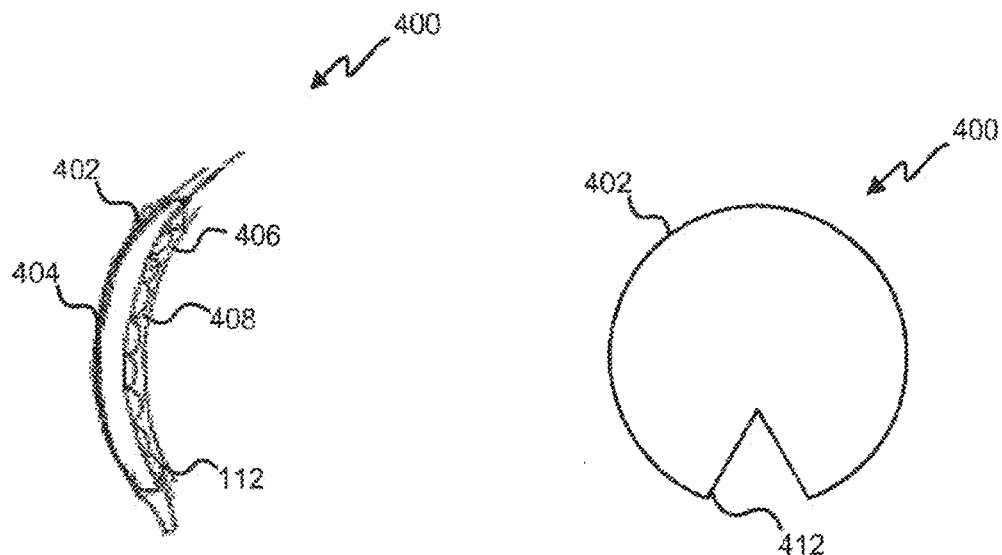
Fig. 4A
Fig. 4B
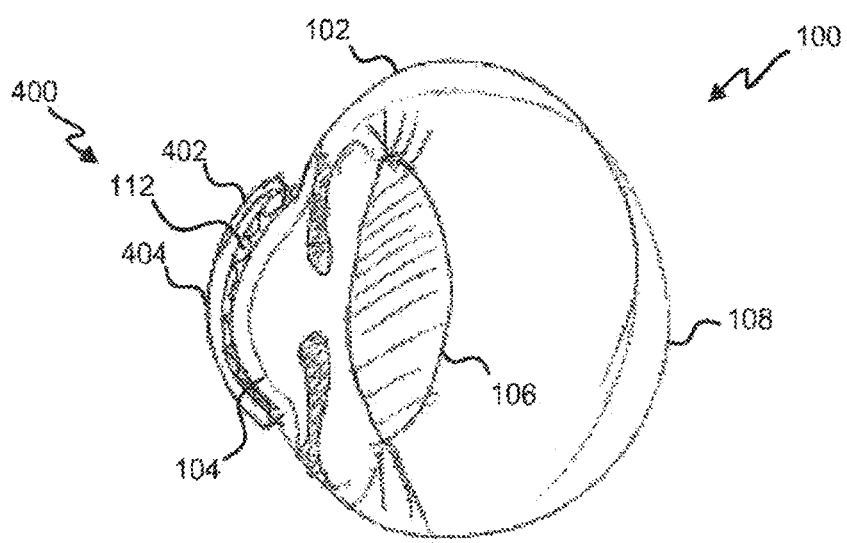
Fig. 4C

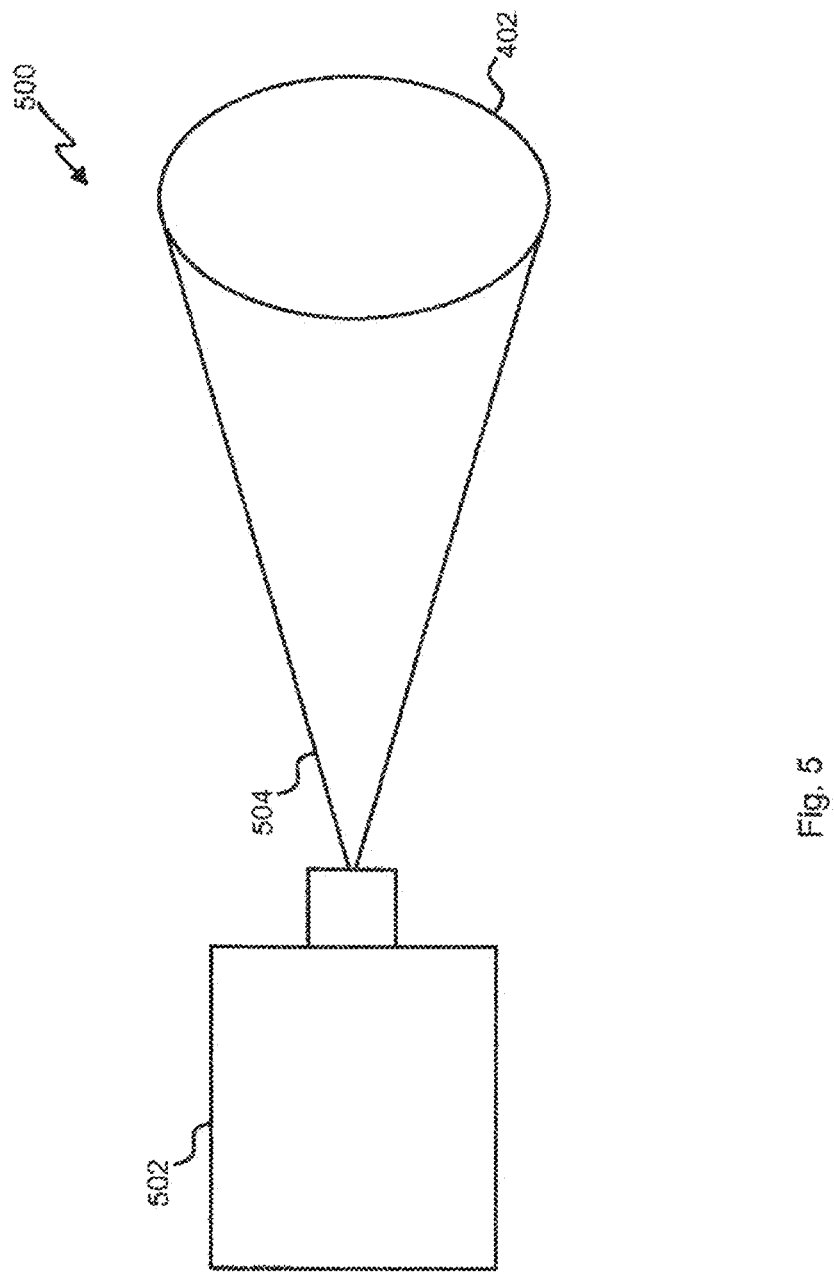

NON-INVASIVE REFRACTIVE TREATMENT USING NANOPARTICLES

CROSS-REFERENCES TO RELATED APPLICATIONS

This application is a continuation of and claims priority to U.S. patent application Ser. No. 14/199,766, filed Mar. 6, 2014, which claims priority to U.S. Provisional Application No. 61/794,070, filed on Mar. 15, 2013, the entire contents of which are incorporated herein by reference.

FIELD OF THE INVENTION

Embodiments of the present invention generally relate to optical treatment and more particularly to non-invasive refractive treatment method based on sub wavelength particle implantation.

BACKGROUND OF THE INVENTION

Non-spectacle, non-contact lens refractive correction generally involves the use invasive surgical techniques that require a healing period, may reduce the integrity of the cornea, and which can lead to undesired side effects such as night halos, dry eye syndrome, and increased higher order aberrations. A new refractive treatment method based on sub wavelength particle implantation can accomplish similar treatments with far less invasive procedures and no appreciable weakening of the cornea.

SUMMARY OF THE INVENTION

The field of the invention relates to systems and methods for optical treatment and more particularly to non-invasive refractive treatment method based on sub wavelength particle implantation. In an embodiment, a method for optical treatment identifies an optical aberration of an eye, determines a dopant delivery device configuration in response to the optical aberration of the eye, wherein the determined dopant delivery device is configured to impose a desired correction to the eye to mitigate the identified optical aberration of the eye by applying a doping pattern to the eye so as to locally change a refractive index of the eye.

Other systems, methods, features, and advantages of the invention will be or will become apparent to one with skill in the art upon examination of the following drawings and detailed description. It is intended that all such additional systems, methods, features, and advantages be included within this description, be within the scope of the invention, and be protected by the accompanying claims.

BRIEF DESCRIPTION OF THE DRAWINGS

The present disclosure is described in conjunction with the appended figures:

FIGS. 4A-4C are schematic illustrations of one embodiment of a contact lens dopant delivery system;

FIG. 5 is a schematic depict embodiments of a dopant delivery configuring system.

Figure 1:
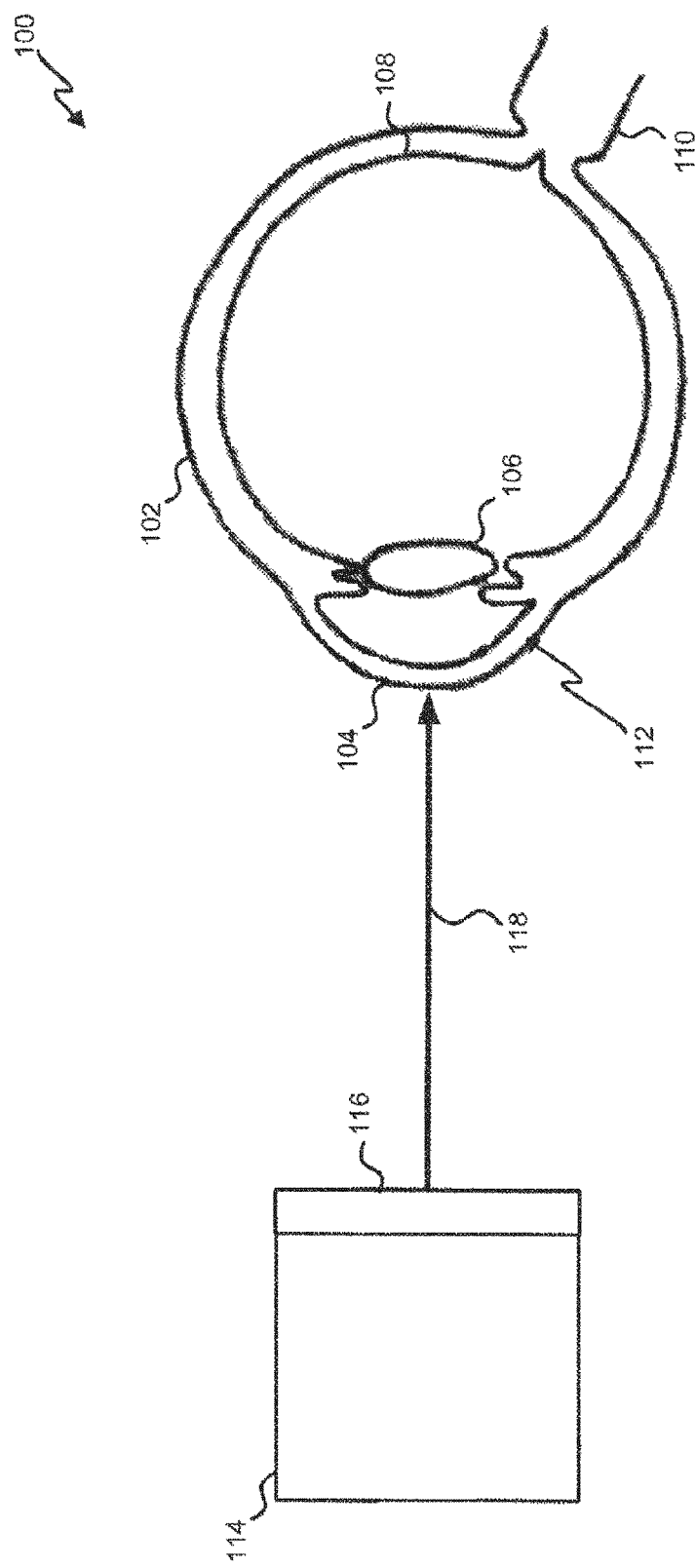
FIG. 1 is a schematic illustration of one embodiment of a non-invasive refractive treatment system.

In the appended figures, similar components and/or features may have the same reference label. Where the reference label is used in the specification, the description is applicable to any one of the similar components having the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label

DETAILED DESCRIPTION OF THE INVENTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

In some embodiments, noninvasive refractive treatment can modify the refractive index of the eye, and specifically the corneal refractive index, rather than reshape the cornea to affect a refractive correction. This change in the corneal refractive index can be accomplished through the application of various dopants to the cornea that can include, for example, one or several chemicals and/or nanoparticles.

The nanoparticles can be metallic, and can enhance the index of refraction through surface plasmon effects, and/or the bulk material from which the nanoparticles are made can be absorptive when in bulk form. The nanoparticles may contain inorganic, high index of refraction, transparent materials such as, for example, $ZrO_2$ embedded in inorganic polymers. The nanoparticles and/or their host material can be tailored to bond with specific cell organelles or structures to resist diffusion.

In some embodiments in which nanoparticles are applied to the cornea, the nanoparticles can have a size that is smaller than, and in some embodiments, much smaller than the wavelength of visible light. In some embodiments in which nanoparticles are applied to the cornea, the nanoparticles can have an index of refraction that is different than the index of refraction of the cornea, and in some embodiments, the nanoparticles can have an index of refraction that is substantially different than the index of refraction of the cornea.

The implantation of nanoparticles having an index of refraction different than that of the cornea can result in a change in the local index of refraction of the cornea in proportion to the number of nanoparticles implanted in a given volume of the cornea, or in other words, the density of the implanted nanoparticles. In some embodiments, the density and/or lateral distribution of the nanoparticles can vary across the cornea of the eye, which variance can result in a varying index of refraction across the cornea of the eye. This varying index of refraction across the cornea of the eye, caused by the unequal distribution of the nanoparticles, allows treatment of optical aberrations including, myopia, hyperopia, astigmatism, mixed astigmatism, and/or any other lower or higher order aberrations.

In some embodiments, the dopant applied to the cornea to affect the change in the refractive index of the cornea can have a variety of interactions with the corneal tissue. In some embodiments, for example, these dopants can be nonreactive with the corneal tissue and merely be suspended within the corneal tissue, and specifically, in some embodiments, within the corneal stroma, and in some embodiments, these dopants can bind with corneal tissue to thereby secure their position within the cornea. In some embodiments, nanoparticle materials can be selected to be biocompatible with the tissue of the cornea and/or to chemically bond to the corneal tissue. In some embodiments in which nanoparticles are used for altering the index of refraction of the cornea, nanoparticles as small as, for example, 1 nanometer, 5 nanometers, 10 nanometers, 20 nanometers, 30 nanometers, 50 nanometers, 100 nanometers, 500 nanometers, and/or any other desired or intermediate size can be used. In some embodiments, particles can be size so as to allow painless placement in the cornea and so as to prevent light scatter.

Insertion of dopants including, for example, one or several chemicals and/or one or several nanoparticles, into the cornea can be achieved using a variety of techniques. In some embodiments, for example, the dopants can be inserted into the cornea via high velocity impingement on the exterior surfaces of the cornea. In some embodiments, for example, the velocity of the dopants can be configured so as to allow penetration to the desired depth into the cornea. In some embodiments, for example, the dopants can be inserted into the cornea via diffusion. In some embodiments, the dopants can be configured such that they diffuse to the proper depth within the cornea, and then maintain their position at that desired depth.

With reference now to FIG. 1, a schematic illustration of one embodiment of a noninvasive refractive treatment system 100 is shown. The noninvasive refractive treatment system 100 can provide noninvasive refractive treatment to a patient. Advantageously, such treatments allow short recovery periods, can be repeated and/or adjusted based on future changes to the patient's eye, and/or can compensate for over and/or under treatment in a previous procedure.

The noninvasive refractive treatment system 100 includes an eye 102. The eye 102 can be any eye, and can be, for example, a human eye. The eye 102 includes the cornea 104, the lens 106, the retina 108, and the optic nerve 110. In the embodiment depicted in FIG. 1, a plurality of dopants 112 have been deposited with in the cornea 104 of the eye 102. In some embodiments, these dopants can be, for example, nanoparticles.

As further seen in FIG. 1, the noninvasive refractive treatment system 100 can include a dopant delivery system 114. In some embodiments, the dopant delivery system 114 can be configured to measure the aberration of the eye 102, determine a dopant profile for compensating and/or correcting for the aberration, and to deliver dopant to the eye 102, and specifically to the cornea 104 of the eye 102.

In some embodiments, the dopant delivery system 114 includes a dopant delivery device 116 that delivers the dopant 112 to the eye 102. In some embodiments, the dopant delivery device 116 can include features configured to accelerate the dopant to a desired velocity to allow penetration of the dopant to a desired depth into the cornea 104. In such an embodiment, the dopant delivery system 114 can control the dopant delivery device and can further include features configured to calculate the necessary penetration velocity of the dopant. This process can include determining a property of the cornea 104 such as, for example, the elasticity, thickness, toughness, and/or any other property relevant to penetration of dopant into the cornea 104, and using this property in combination with the mass of the dopant to determine the velocity for dopant penetration to a desired depth to the cornea 104.

In some embodiments, the insertion of the dopant 112 into the cornea 104 can be facilitated by one or several piezo-electric transducers. In some embodiments, the dopant 112 can be ionized, and can be accelerated to the desired velocity for dopant insertion into the cornea 104.

As seen in FIG. 1, the dopant 112 can be delivered 118 from the dopant delivery device 116 to the cornea 104. In embodiments in which the dopant 112 is delivered to the cornea 104 at a penetrating velocity, the direction of the velocity of the dopant 112 can be calculated and/or controlled to allow insertion of the dopant 112 into desired portions of the cornea. In some embodiments, for example, the same techniques used to accelerate the dopant 112 can be further used to control the direction of the velocity of the dopant 12.

In some embodiments, dopant delivery system 114 can be used in connection with other devices and components that can, for example, measure the aberration of the eye 102, perform calculations relating to the aberration of the eye 102, and/or configure the dopant delivery device 114. These other devices and/or components can be integrated within the non-invasive refractive treatment system 100.

Figure 1A:
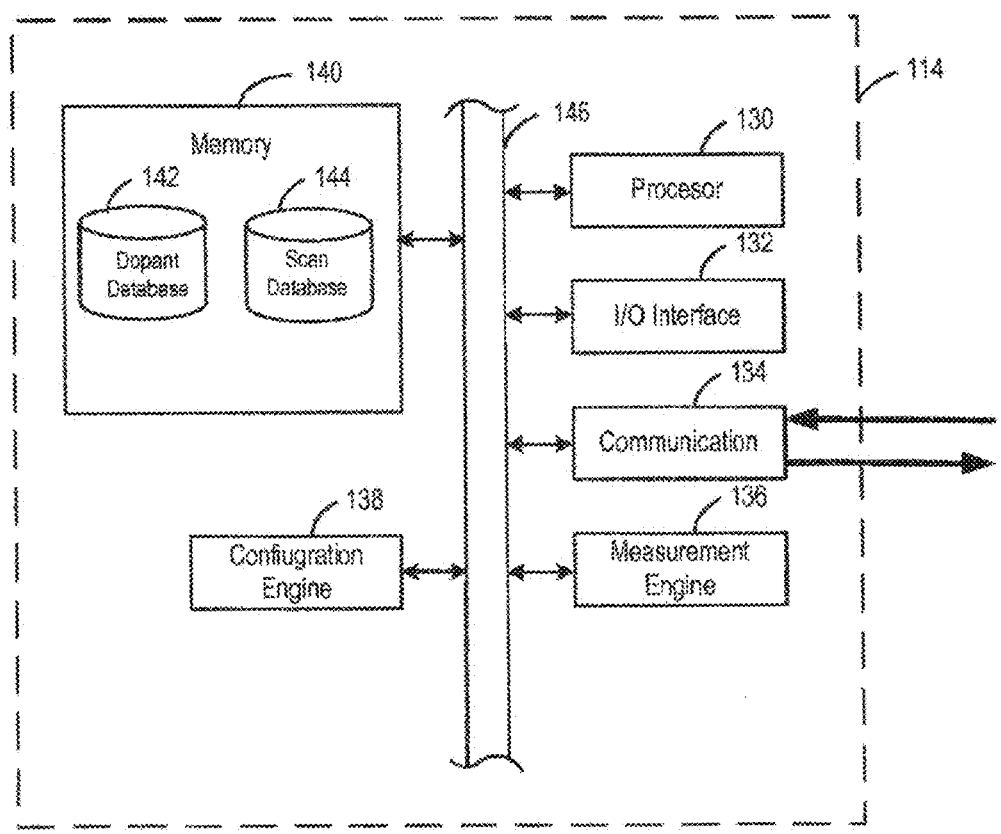
FIG. 1A is a schematic illustration of one embodiment of a dopant delivery device.

With reference now to FIG. 1A, a schematic illustration of one embodiment of the dopant delivery system 114 is shown. The dopant delivery system 114 can be configured to deliver dopant 112 to the eye 102. In some embodiments, the dopant delivery system 114 includes a processor 130. The processor 130 can provide instructions to, and receive information from the other components of the dopant delivery system 114. The processor 130 can act according to stored instructions to control the other components of the dopant delivery system 114. The processor 200 can comprise a microprocessor, such as a microprocessor from Intel® or Advanced Micro Devices, Inc.®, or the like.

The dopant delivery system 114 can include an input/output interface 132. The input/output interface 132 communicates information, including outputs, to, and receives inputs from a user. The input/output interface 132 can include a screen, a speaker, a monitor, a keyboard, a microphone, a mouse, a touchpad, a keypad, and/or any other feature or features that can receive inputs from a user and provide information to a user. In some embodiments, the input/output interface 132 can provide outputs to, and receive inputs from a user including a doctor. In some embodiments, the input/output interface 132 can be configured to allow the user including the doctor to control the operation of the dopant delivery system 114, and to specifically control the interaction of the dopant delivery system 114 with the patient.

The dopant delivery system 114 can comprise a communication engine 134. The communication engine 134 can allow the dopant delivery system 114 to communicatingly connect with other devices, and can allow the dopant delivery system 114 to send and receive information from other devices. The communication engine 134 can include features configured to send and receive information, including, for example, an antenna, a modem, a transmitter, a receiver, or any other feature that can send and receive information. The communication engine 134 can communicate via telephone, cable, fiber-optic, or any other wired communication network. In some embodiments, the communication engine 134 can communicate via cellular networks, WLAN networks, or any other wireless network.

The dopant delivery system 114 includes a measurement engine 136. In some embodiments, for example, the measurement engine 136 can be configured to measure aberration data relating to the eye 102. The measurement engine 136 can use any technique and/or desired features to measure the aberration relating to the eye 102. In some embodiments, the measurement engine 136 can include a phoroptor and/or aberrometer.

The dopant delivery system 114 can include a configuration engine 138. In some embodiments, the configuration engine 138 can include features that can configured the dopant delivery device 116 for delivering the dopant 112 to the eye 102. In some embodiments, the configuration engine 138 can comprise an activation device. The activation device will be discussed in greater detail below.

The dopant delivery system 114 can include memory 140. The memory 140 can include stored instructions that, when executed by the processor 130, control the operation of the dopant delivery system 114.

In some embodiments, the memory 140 can include a dopant database 142. The dopant database 142 can include information relating to the dopant 112 such as, for example, information relating to the effect of the dopant on the index of refraction of the eye 102, doping patterns that can be used as corrections for optical aberrations, and information relating to the configuration of the dopant delivery device 114.

The memory 140 can include a scan database 144. The scan database 144 can include data generated by the measurement engine 134. This information can relate to the aberration the eye 102, refractive state of the eye 102 after performing the noninvasive refractive treatment.

The dopant delivery system 114 can include a feature 146 communicatingly linking all of the components of the dopant delivery system 114. In some embodiments, this feature 146 can comprise, for example, a bus.

Figure 2A:
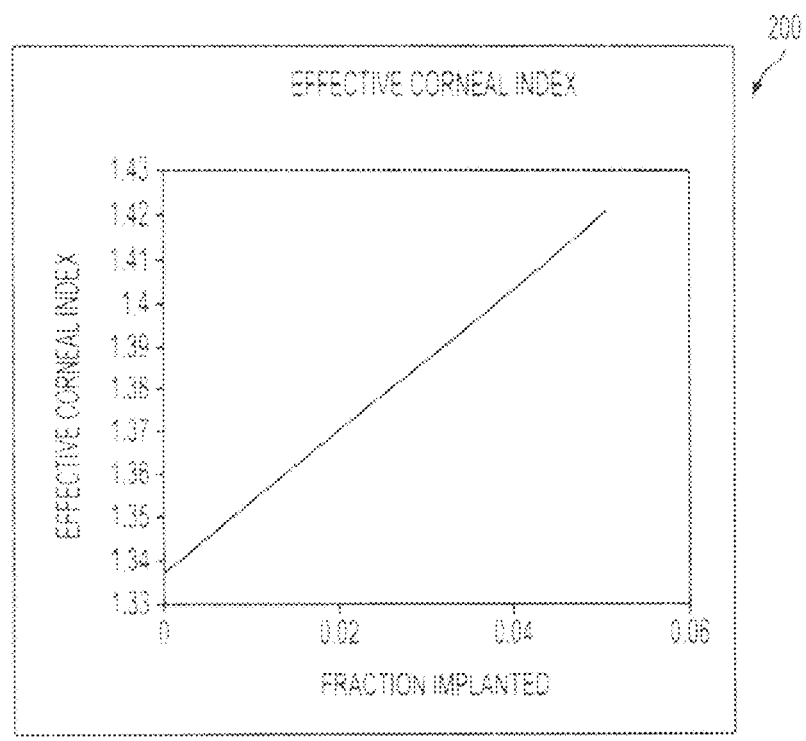
FIGS. 2A-2B are graph's depicting changes in refractive properties of an eye caused by the implantation of a dopant in the eye.
Figure 2B:
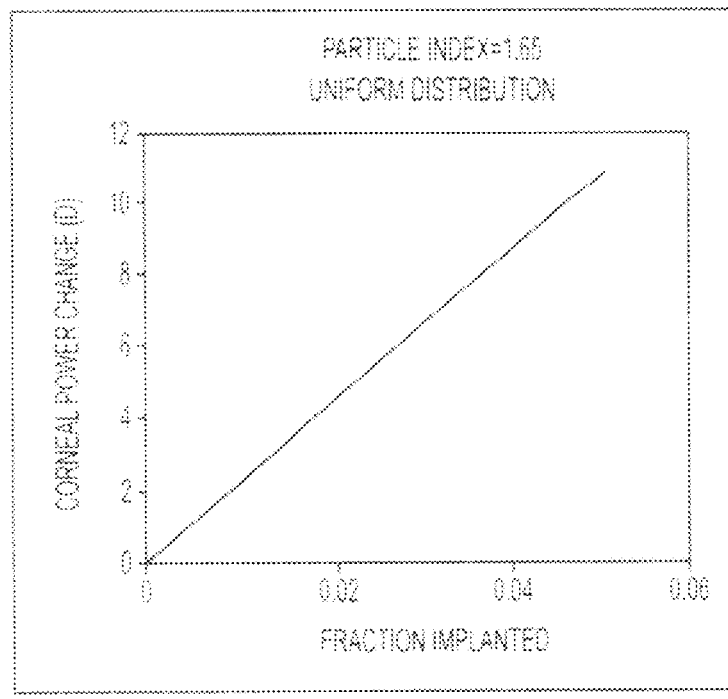

With reference now to FIGS. 2A-2B, graph's depicting changes in refractive properties of an eye 102 caused by the implantation of a dopant 112 in the eye 102 are shown. Specifically, the graphs depict the impact of the uniform implantation of nanoparticles having a refractive index higher than the refractive index of the cornea into the corneal tissue. Specifically, FIG. 2A includes graph 200 which depicts the effective corneal index as a function of the implanted fraction of dopant 112, and FIG. 2B includes graph 202 which depicts the corneal power change as a function of the implanted fraction of dopant 112.

As seen in FIGS. 2A-2B, the nominal corneal effective refractive index is approximately 1.337. Further, the mean human corneal radius of curvature is approximately 7.8 mm. The combination of the nominal corneal effective refractive index and the mean human corneal radius of curvature results in an effective corneal power of approximately 43.2 diopters. The above figures depict the change in the effective corneal index and corneal power resulting from the implantation of nanoparticles having an index of refraction of 1.65. As seen in FIGS. 2A-2B, as the fractional percent of implanted nanoparticles increases, the effective corneal index likewise increases, and the corneal power changes. For example, and based on FIGS. 2A-2B, when the fraction of nanoparticles implanted reaches 1%, the local index of refraction increases to 1.35 and the corneal power increases by approximately 2.1 dpt.

Figure 3:
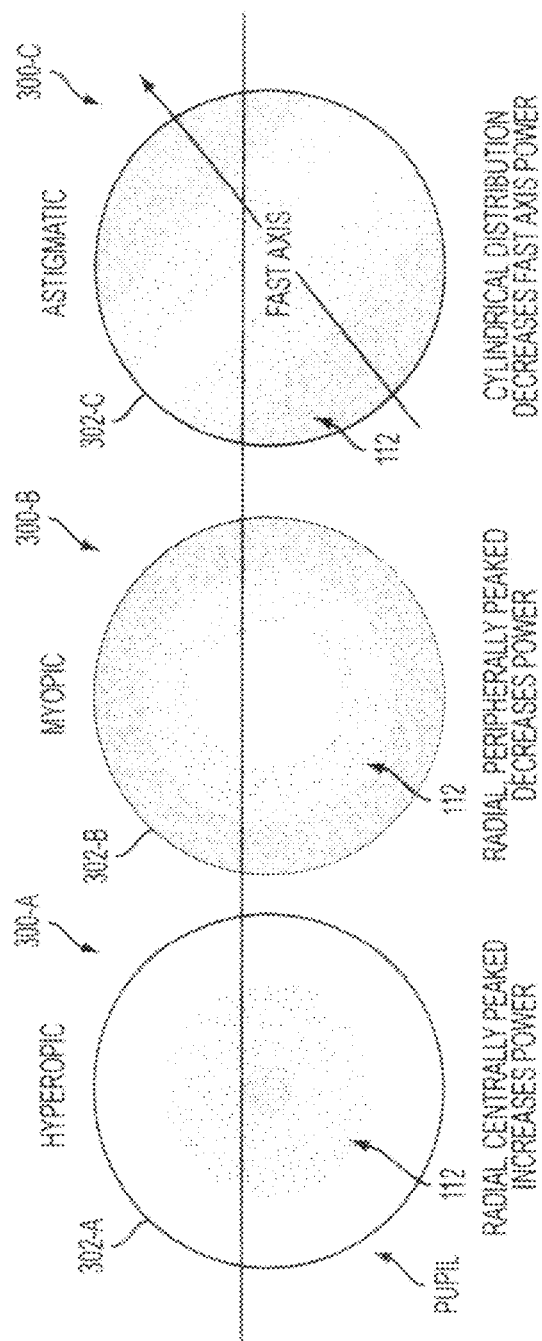
FIG. 3 is a schematic illustration of embodiments of dopant distribution in the eye.

With reference now to FIG. 3, a schematic illustration of embodiments of dopant 112 distribution in the eye 102 is shown. In some embodiments, the dopant 112 distributions in the eye 102 shown in FIG. 3 can comprise non-uniform distribution patterns. These non-uniform distribution patterns can be used in the treatment of specific refractive problems. Non-uniform distributions can effectively lead to a graded index of refraction useful for treating all the common refractive conditions, in some cases with reduced implant rates.

FIG. 3 depicts a first distribution pattern 300-A occurring in the first pupil 302-A. In this first distribution pattern 300-A, dopant 112 is concentrated in the center of the pupil 302-A. In some embodiments, the concentration of dopant 112 in the center the pupil 302-A, and specifically lateral distributions of high index particles concentrated at the center of the pupil 302-A can be used to increase the corneal power for treating hyperopia.

FIG. 3 depicts a second distribution pattern 300-B occurring in the second pupil 302-B. In the second distribution pattern 300-B, dopant 112 is concentrated radially around the periphery of the pupil 302-B. In some embodiments, the concentration of dopant 112 around the radial periphery of the pupil 302-B, and specifically lateral distributions with a minimum number of particles at the pupil center can be used to reduce the corneal power and thereby treat myopia.

FIG. 3 depicts a third distribution pattern 300-C occurring in the third pupil 302-C. In the third distribution pattern 300-C, dopant 112 is cylindrically distributed perpendicular to the fast axis of the pupil 302-C. In some embodiments, the cylindrical distribution perpendicular to the fast axis of the pupil 302-C, and/or an elliptical distribution can be used to treat astigmatism.

Similarly, other dopant distribution patterns can be used to treat other optical aberrations including, for example, higher order aberrations. Specifically, higher order aberrations can be treated through other non-uniform particle distribution patterns.

With reference now to FIGS. 4A-4C, schematic illustrations of one embodiment of a contact lens dopant delivery system 400 are shown. The contact lens dopant delivery system 400 is a subset of the dopant delivery device 116. In some embodiments, the contact lens dopant delivery system 400 can be configured to deliver dopant 112 to the eye 102, and specifically to the cornea 104 of the eye 102. In some embodiments, the contact lens dopant delivery system 400 can be configured for placement on a portion of the eye 102 such as, for example, on top of the cornea 104 of the eye 102. In some embodiments, the contact lens dopant delivery system 400 can include dopant 112 embedded and/or applied onto portions of the contact lens dopant delivery system 400.

In some embodiments, the dopant 112 can be uniformly distributed throughout the contact lens 402, so as to allow the customization of the contact lens 402 to treat a range of desired aberrations. In some embodiments, the dopant 112 can be non-uniformly distributed throughout the contact lens 402. In some such embodiments, the non-uniform distribution of dopant 112 can allow the pre-configuration of the contact lens for treatment of a specific type and/or strength of aberration. In embodiments in which the dopant 112 is pre-distributed throughout the contact lens 402 to allow the treatment of a specific type and/or strength of aberration, the contact lens dopant delivery system 100 can comprise one or several contact lenses 402 which can be applied to the eye, singly, or in succession to treat a specified aberration including, for example, a type and a strength of aberration.

This dopant 112 can be transferred to the eye 102, and specifically to the cornea 104 of the eye when the contact lens dopant delivery system 400 is placed on the eye 102.

With reference now to FIG. 4A, a side view of one embodiment of the contact lens dopant delivery system 400 is shown. The contact lens dopant delivery system 400 includes a contact lens 402 that can comprise a variety of shapes and sizes. In some embodiments, for example, the contact lens 402 can be sized to cover and/or substantially cover the cornea 104. In some embodiments, the contact lens 402 can comprise a variety of materials. In some embodiments, for example, the contact lens 402 can comprise a biocompatible material.

The contact lens 402 comprises a front 404 and an opposing back 406. In some embodiments, the contact lens 402 can comprise a convex shape configured for placement onto the cornea 104 of the eye 102, which shape can advantageously increase the contact area of the back 406 of the contact lens 402 with the cornea 104 of the eye 102. In some embodiments, for example, all or portions of the contact lens 402 can comprise a dopant carrier 408. In some embodiments, the dopant carrier 408 can be configured to releasably contain the dopant 112. In some embodiments, for example, the dopant carrier 408 can be configured to retain the dopant 112 in the contact lens 402 unless the dopant 112 is activated, which activation can allow the dopant 112 to be released from the contact lens 402, and specifically from the dopant carrier 408 of the contact lens 402. In some embodiments, for example, the activation of the dopant 112 can comprise a change in the shape, composition, and/or properties of the dopant and/or the dopant carrier 408.

With reference now to FIG. 4B, a front view of one embodiment of the contact lens delivery system 400 is shown. As seen in FIG. 4B, the contact lens 402 can comprise a circular shape when viewed from the front. In some embodiments, the contact lens 402 can comprise an orienting feature 412. This orienting feature 412 can advantageously facilitate in orienting the contact lens 402 on the eye 102. This can allow use of the contact lens dopant delivery system 400 in the treatment of astigmatism and/or higher order aberrations. In some embodiments, the orienting feature 412 can be configured to automatically orient the contact lens 402 on the eye 102 such as, for example, when the patient blinks their eye 102.

With reference now to FIG. 4C, side view of one embodiment of the noninvasive refractive treatment system 100 is shown. In this embodiment, the contact lens delivery system 400 is shown placed on the eye 102 so that the back 406 of the contact lens 402 is contacting the cornea 104 of the eye 102. In this embodiment, activated dopant 112 can be delivered to the cornea 104 of the eye 102, which delivery can affect a change in the index of refraction of the cornea 104 and thereby alter a refractive property of the eye 102. In embodiments in which the dopant 112 is activated according to a doping pattern configured to compensate for an optical aberration of the eye, the activated dopant 112 can remedy and/or provide for the noninvasive treatment of the optical aberration of the eye 102.

With reference now to FIG. 5, a schematic illustration of one embodiment of a dopant delivery configuration system 500 is shown. In some embodiments, for example, the dopant delivery configuration system 500 can comprise the contact lens 402 and an activation device 502. The dopant delivery configuration system 500 can be configured to activate the dopant 112 in and/or on the contact lens 402 so as to allow the delivery of the dopant 112 to the cornea 104 of the eye 102.

The activation device 502 can comprise any device configured to activate the dopant 112 by changing the shape, composition, and/or properties of the dopant 112 and/or the dopant carrier 408. In some embodiments, for example, the activation device 502 can activate the dopant via the irradiation of the contact lens 402 including, for example, the dopant 112 and/or the dopant carrier 408, the application of one or several chemicals to the contact lens 402 including, for example, the dopant 112 and/or the dopant carrier 408, and/or via the mechanical interaction with the contact lens 402 including, for example, the dopant 112 and/or the dopant carrier 408. As seen in FIG. 5, the activation device 502 is interacting 504 with the contact lens 402 so as to activate the dopant 112. In some embodiments, this interaction 504 can be controlled so that desired portions of the dopant 112 are activated and so that other portions of the dopant 112 are not activated. Advantageously, selective activation of portions of the dopant 112 on the contact lens 402 can allow treatment of different aberrations including, for example, lower order aberrations and/or higher order aberrations.

Figure 6:
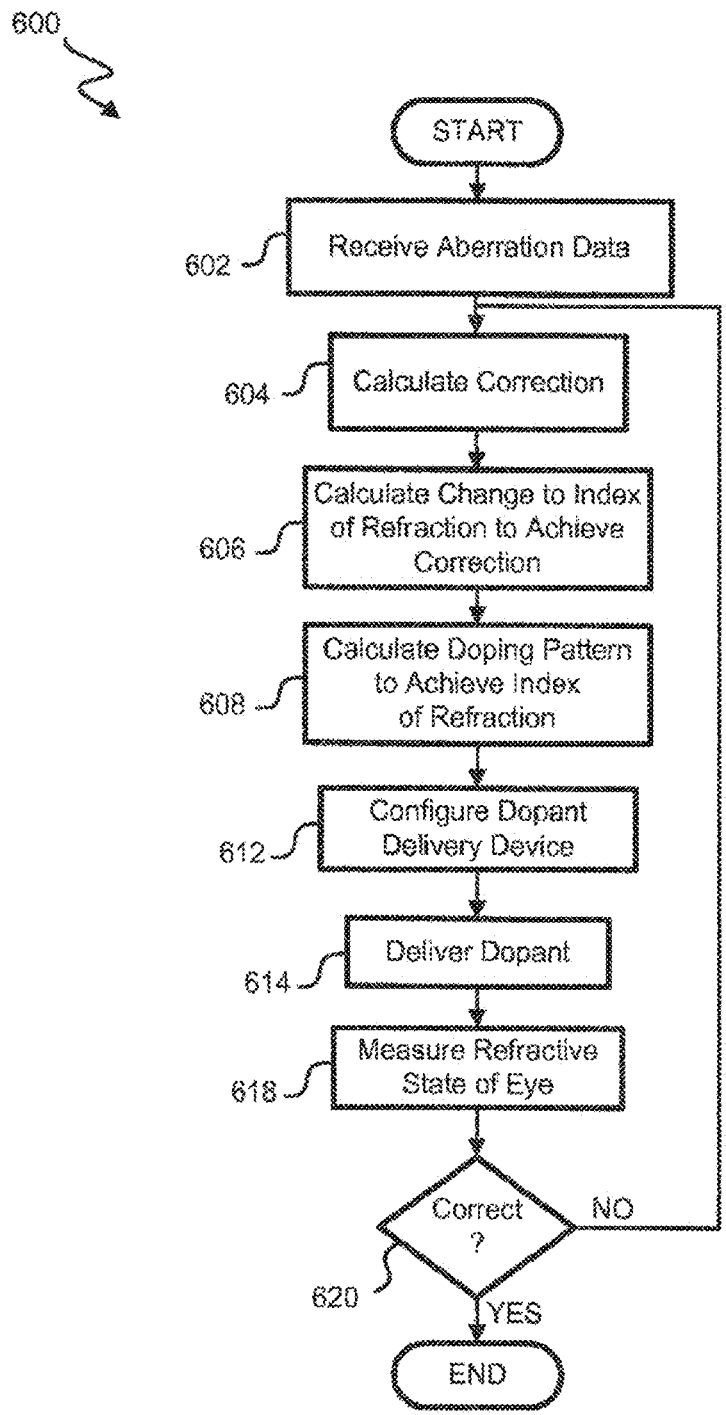
FIG. 6 is a flowchart illustrating one embodiment of a process for non-invasive refractive treatment.

With reference now to FIG. 6, a flowchart illustrating one embodiment of a process 600 for noninvasive refractive treatment is shown. In some embodiments, this process 600 can be used to provide dopant 112 to portions of the eye 102 including, for example, to the cornea 104. In some embodiments, the process 600 can be performed using noninvasive refractive treatment system 100, and specifically the dopant delivery system 114, the contact lens delivery system 400, and/or the activation device 502.

The process 600 can begin at block 602 wherein aberration data is received. In some embodiments, for example, the aberration data can be received from any device capable of identifying and/or detecting optical aberration in an eye 102. In some embodiments, for example, the aberration data can be received from a phoroptor, an aberrometer, and/or any other desired device capable of collecting this data, and in some embodiments, this information can be received from the measurement engine 136 and/or any component of the measurement engine 136. In some embodiments, this information can be generated by component other than the dopant delivery system 114 and can be communicated to the noninvasive refractive treatment system via the communication engine 134. In some embodiments, the received aberration data can be stored in the memory 140 including, for example the scan database 144.

After the aberration data is collected, the process 600 proceeds to block 604 wherein the correction for the collected aberration data is calculated. In some embodiments, the calculation of the correction can be performed by a component of dopant delivery system 114, and in some embodiments, the calculation of the correction can be performed by a component and/or device other than the dopant delivery system 114. In some embodiments, for example, the correction can be calculated by a component of the dopant delivery system 114 including, for example, the processor 130. In some embodiments, the correction can be calculated with inputs regarding the details of the anatomy of the eye 102 including, for example, the details of the size and shape of the eye 102 and/or the components of the eye 102. In some embodiments in which a phoropter is used to collect aberration data, the calculation of the correction can be likewise received from the phoropter via, for example, the communications engine 134.

After the correction has been calculated, the process 600 proceeds to block 606 wherein the change in the index of refraction that will result in achieving the correction is calculated. In some embodiments, this calculation can be performed as part of the step performed in block 604 discussed above, in some embodiments, this step can be performed separate from step performed in block 604 discussed above. In some embodiments, this calculation can be performed by components of the dopant delivery system 114, and in some embodiments, this calculation can be performed by components other than those of the dopant delivery system 114. In some embodiments, this calculation can comprise the generation of an index of refraction profile indicating the locations of changes to the index of refraction on the cornea 104 of the eye 102, in the magnitude of the changes to the index of refraction of the cornea 104 of the eye 102.

After the change in the index of refraction is calculated, the process 600 proceeds to block 608 wherein the doping pattern that creates indices of refraction within the cornea 104 corresponding to the index of refraction profile is generated. In some embodiments, the doping pattern can be generated by a component of the dopant delivery system 114 including, for example, the processor 130 and can be based off of information retrieved from the dopant database 142 and the scan database 144. In some embodiments, the doping pattern can include information identifying the location for the placement of dopant 112 on the eye 102, and specifically on the cornea 104 of the eye, and the concentration of the dopant 112 in those locations.

After the doping pattern is been calculated, the process 600 proceeds to block 612 wherein the dopant delivery device 116 is configured. In some embodiments, for example, the configuring of the dopant delivery device 116 can comprise making changes to the dopant delivery device 116 so that the dopant delivery device 116 delivers dopant 112 to portions of the eye 102 including, for example, the cornea 104, specified by the doping pattern. In some embodiments, the dopant delivery device 116 can be configured by the configuration engine 138 and/or a component of the configuration engine. In some embodiments, this component of the configuration engine 148 can include the dopant delivery configuration system 500, and specifically the activation device 502 of the dopant delivery configuration system 500.

After the dopant delivery device has been configured, the process proceeds to block 614 wherein the dopant 112 is delivered. In some embodiments, for example, the dopant 112 can be delivered by the dopant delivery system 114 including, for example, the dopant delivery device 116. In one specific embodiment, the dopant 112 can be delivered by the contact lens delivery system 400 by placement of the contact lens 402 of the contact lens delivery system 400 on the eye 102, and specifically on the cornea 104 of the eye 102.

After the dopant is been delivered, the process 600 proceeds to block 618 wherein the refractive state of the eye 102 can be measured. In some embodiments, this step can be performed in the same manner as that performed in block 602 above, and the information measured in this step can be used to determine the success of the noninvasive refractive treatment.

After the refractive student the eye 102 has been measured, the process 600 proceeds to decision state 620 wherein it is determined if the measured refractive state of the eye 102 corresponds with the correct refractive state of the eye. In some embodiments, this determination can be made by the processor 130 of the dopant delivery system 114 based on the comparison of the outcome calculated from the collected aberration data and the calculated correction, and the measured refractive state of the eye. If it is determined that the measured refractive state of the eye 102 does not correspond with the desired outcome of the noninvasive refractive treatment, then the process 600 returns to block 604. If it is determined that the measured refractive state of the eye 102 does correspond with the desired outcome of the noninvasive refractive treatment, then the process can terminate.

A number of variations and modifications of the disclosed embodiments can also be used. Specific details are given in the above description to provide a thorough understanding of the embodiments. However, it is understood that the embodiments may be practiced without these specific details. For example, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A method for optical treatment, the method comprising:
   identifying an optical aberration of an eye,
   determining a dopant delivery device configuration in response to the optical aberration of the eye to impose a desired correction to change an index of refraction of cornea of the eye to mitigate the identified optical aberration of the eye by delivering a dopant according to a doping pattern to cornea of the eye, wherein the delivered dopant locally changes refractive index values of the cornea without reshaping the cornea, and
   configuring the dopant delivery device as determined, wherein configuring the dopant delivery device comprises activating the dopant located on first portions of a contact lens by a selective irradiation of the first portions of the dopant delivery device.

2. The method of claim 1, further comprising calculating the doping delivery device configuration in response to the optical aberration of the eye, the optical aberration of the eye comprising a high-order optical aberration, and wherein calculating the doping delivery device configuration comprises a location and concentration for dopant application to the eye.

3. The method of claim 1, wherein the optical aberration of the eye comprises one of a myopia, a hyperopia, and a regular astigmatism.

4. The method of claim 1, wherein the optical aberration of the eye comprises a higher order aberration.

5. The method of claim 1, wherein dopant located on second portions of the contact lens is not activated.

6. The method of claim 5, wherein the contact lens comprises an orienting feature configured to orient the contact lens on the eye.

7. The method of claim 1, wherein the dopant located on portions of the contact lens is configured to diffuse into the cornea.

8. The method of claim 1, wherein the dopant is configured to implant in the corneal stroma.

9. The method of claim 8, wherein the dopant comprises a plurality of nanoparticles.

10. A method of providing non-invasive optical correction to an eye comprising:
    identifying the optical aberration of the eye;
    calculating a doping pattern configured to compensate for the optical aberration of the eye, wherein the doping pattern comprises a description of the location and concentration for dopant application to the cornea of the eye;
    configuring a dopant delivery system according to the calculated doping pattern, wherein configuring the dopant delivery device comprises activating dopant located on first portions of a contact lens by a selective irradiation of the first portions of the dopant delivery device; and
    delivering dopant to the cornea of the eye according to the calculated doping pattern, wherein the delivered dopant locally changes refractive index values of the cornea without reshaping the cornea.

11. The method of claim 10 further comprising calculating a corrective change to the index of refraction of the eye, wherein the change in the index of refraction compensates for the identified optical aberration of the eye.

12. The method of claim 11, wherein the doping pattern is calculated from the corrective change to the index of refraction of the eye.

13. The method of claim 10, wherein the dopant delivery system comprises a contact lens carrying dopant.

14. The method of claim 10, wherein configuring the dopant delivery system comprises applying dopant to portions of the contact lens identified by the doping pattern.

15. The method of claim 10, wherein dopant located on second portions of the contact lens is not activated.

16. The method of claim 15, wherein the contact lens comprises an orienting feature configured to orient the contact lens on the eye.

17. The method of claim 10, wherein the dopant located on portions of the contact lens is configured to diffuse into the cornea.

18. The method of claim 10, wherein the dopant is configured to implant in the corneal stroma.

19. The method of claim 18, wherein the dopant comprises a plurality of nanoparticles.

* * * * *